United States Patent [19]

Chou

[11] Patent Number: 4,774,364
[45] Date of Patent: Sep. 27, 1988

[54] INTEGRATED ALKYLATION/ALKYL TERTIARY-ALKYL ETHER SYNTHESIS PROCESS

[75] Inventor: Tai-Sheng Chou, Sewell, N.J.

[73] Assignee: Mobil Oil Corporation, New York, N.Y.

[21] Appl. No.: 105,433

[22] Filed: Oct. 7, 1987

[51] Int. Cl.$^4$ ............................................. C07C 41/06
[52] U.S. Cl. .................................... 568/697; 585/722; 585/311
[58] Field of Search ................. 568/697; 585/722, 311

[56] References Cited

U.S. PATENT DOCUMENTS 4,384,161  5/1983  Huang ................................. 585/722
4,605,787  8/1986  Chu et al. ............................ 568/697

Primary Examiner—Howard T. Mars
Attorney, Agent, or Firm—Alexander J. McKillop; Michael G. Gilman; Dennis P. Santini

[57] ABSTRACT

A process is disclosed for the preparation of alkyl tertiary-alkyl ether concurrent with the alkylation of isoparaffins with olefins. The composite zeolite catalyst is reactivated in the alkyl tertiary-alkyl ether synthesis reactor.

13 Claims, 1 Drawing Sheet

INTEGRATED ALKYLATION/ALKYL TERTIARY-ALKYL ETHER SYNTHESIS PROCESS

BACKGROUND OF THE INVENTION

This invention relates to the art of improving octane rating of premium gasolines by providing a novel process for concurrently preparing two octane-enhancing blending components. The first product, alkylate, is prepared by the addition of an olefin to an isoparaffin. The second product, an alkyl tertiary-alkyl ether is prepared by reacting a primary alcohol with an olefin having a double bond on a tertiary carbon atom. This process allows refinery streams of relatively low value to be reacted to form two valuable blending components for premium gasoline. In industry practice an olefin having two to five carbon atoms would be reacted with isobutane in the presence of an acidic catalyst to produce the higher molecular weight alkylate product.

Recent safety and environmental concerns regarding the handling of hydrofluoric acid have prompted the industry to explore heterogeneous alkylation alternatives for replacing strong acid (e.g. HF) alkylation units. One drawback of the heterogeneous alkylation process is the requirement of frequent reactivations of the aged zeolite catalyst. Laboratory reactivation of the aged zeolite catalyst requires a polar solvent (e.g. methanol) extraction followed by a hydrocarbon extraction.

DESCRIPTION OF THE PRIOR ART

U.S. Pat. No. 4,605,787 teaches the preparation of alkyl tert-alkyl ethrs by reacting a primary alcohol with an olefin having a double bond on a tertiary carbon atom in the presence of a zeolite catalyst.

Heterogeneous alkylation using catalyst comprising zeolite Beta and $BF_3$ (e.g. U.S. Pat. No, 4,384,161) experienced deactivation due to hydrocarbon plugging of the zeolite catalyst pores. The aged catalyst was regenerated by polar solvent (e.g. methanol) extraction followed by a hydrocarbon extraction.

U.S. Pat. Nos. 4,605,787 and 4,384,161, cited above, are hereby incorporated by reference as if set forth at length herein.

SUMMARY OF THE INVENTION

In accord with the invention, there has been found a process for the concurrent preparation of alkyl tertiary-alkyl ether and for the alkylation of isoparaffins with olefins in the presence of an acidic zeolite catalyst characterized by having a Constraint Index of about 0.4 to 12, and a silica/alumina ratio of at least about 5.

The members of the class of zeolites useful herein have an effective pore size of generally from about 5 to about 8 angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually pores of large size, e.g. greater than 8 angstroms. The method by which Constraint Index is determined is described fully in U.S. Pat. No. 4,016,218, incorporated herein by reference for details of the method.

Constraint Index (CI) values for some typical materials are:

|  | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-38 | 2 (510° C.) |
| ZSM-48 | 3.5 (538° C.) |
| ZSM-50 | 2.1 (427° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.5–2.0 (316° C.–399° C.) |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 0.4 to 12.

The zeolite catalyst used in heterogenous alkylation requires periodic reactivation. The cycle length varies depending on the process conditions and on the particular catalyst aging characteristics.

The deactivated catalyst must be reactivated to restore its catalytic alkylation activity. In industrial practice, this would necessitate the installation of solvent extraction equipment to accomplish reactivation. One example of such a reactivation process would be polar solvent (methanol) extraction followed by hydrocarbon (hexane) extraction.

Reactivation by solvent extraction is an expense, decreasing the profitability of catalytic alkylation. Solvent extraction also creates a hazardous waste stream which must be disposed of in accordance with the applicable environmental regulations. The most readily apparent advantage of the novel alkylation/alkyl tertiary-alkyl synthesis process is that it replaces the expense of solvent extractive reactivation with the profits derived from the production of an octane-enhancing additive for premium unleaded gasoline. The alkyl tertiary-alkyl ether synthesis reactor provides an environment for hydrocarbon solvent extraction to regenerate the spent alkylation catalyst.

DESCRIPTION OF THE INVENTION

This invention relates to an improved process of reacting an isoparaffin with olefin molecules to provide alkylate in the presence of a Lewis acid and a zeolite catalyst capable of absorbing 2,2,4-trimethylpentane to provide alkylate and then reactivating said catalyst by means of an alkyl tertiary-alkyl ether synthesis reactor. Examples of medium to large pore zeolite catalysts useful in this invention include ZSM-4, ZSM-20, ZSM-3, ZSM-18, zeolite Beta, faujasite, mordenite and zeolite Y.

The synthesis of zeolite Beta and zeolite catalysts ZSM-4, ZSM-20, ZSM-3 and ZSM-18 is taught by U.S. Pat. Nos. 3,308,069; 4,021,447; 3,972,983; 3,415,736 and 3,950,496, respectively, which are incorporated by reference as if set forth at length herein.

FIG. 1 shows the flow diagram of the integrated process for upgrading an isoparaffin-containing aliphatic hydrocarbon stream using zeolite Beta catalyst for both alkylation and alkyl tertiary-alkyl ether synthesis.

In a preferred embodiment, a selective hydrogenation of butadiene (e.g. Engelhard HPN IVB Process) may be incorporated for pretreatment of the alkylation feed. A reduction in the butadiene content for the alkylation unit feed by implementing the selective hydrogenation may reduce the alkylate end point by 50° F. for a sulfuric acid alkylation unit (Oil & Gas Journal, Jan. 17, 1983, P. 103). This suggests that the polymerization reaction of butadiene, which contributes to the heavy alkylate formation, may be detrimental for the zeolite alkylation catalyst having a restricted pore size. The incorporation of the selective hydrogenation of butadiene may extend the cycle length between regenerations. The other added benefits include:

isomerization of butene-1 to butene-2 for an increased alkylate octane number
increased alkylate yield.

Another preferred embodiment of this concept is the incorporation of a feed splitter tower to separate isobutene and butene-1 from the butane-butylene feed stream. This separation scheme allows a reduction in the processing cost for the MTBE synthesis. Such distillation has been practiced commercially (e.g. Hydrocarbon Processing, June 1986, p. 47).

The preferred embodiment of this concept is for slurry reactors (zeolite Beta/$BF_3$ alkylation and zeolite Beta alkyl tertiary-alkyl ether synthesis). While the preferred embodiment employs $BF_3$ as the Lewis acid, this invention contemplates the use of any Lewis acid, including but not limited to the group comprised of $BF_3$, $SbF_5$, and $AlCl_3$. However, moving bed or fixed bed with sequential swing scheme can also be applied using this integrated process.

DETAILED DESCRIPTION OF THE DRAWING

Figure 1:
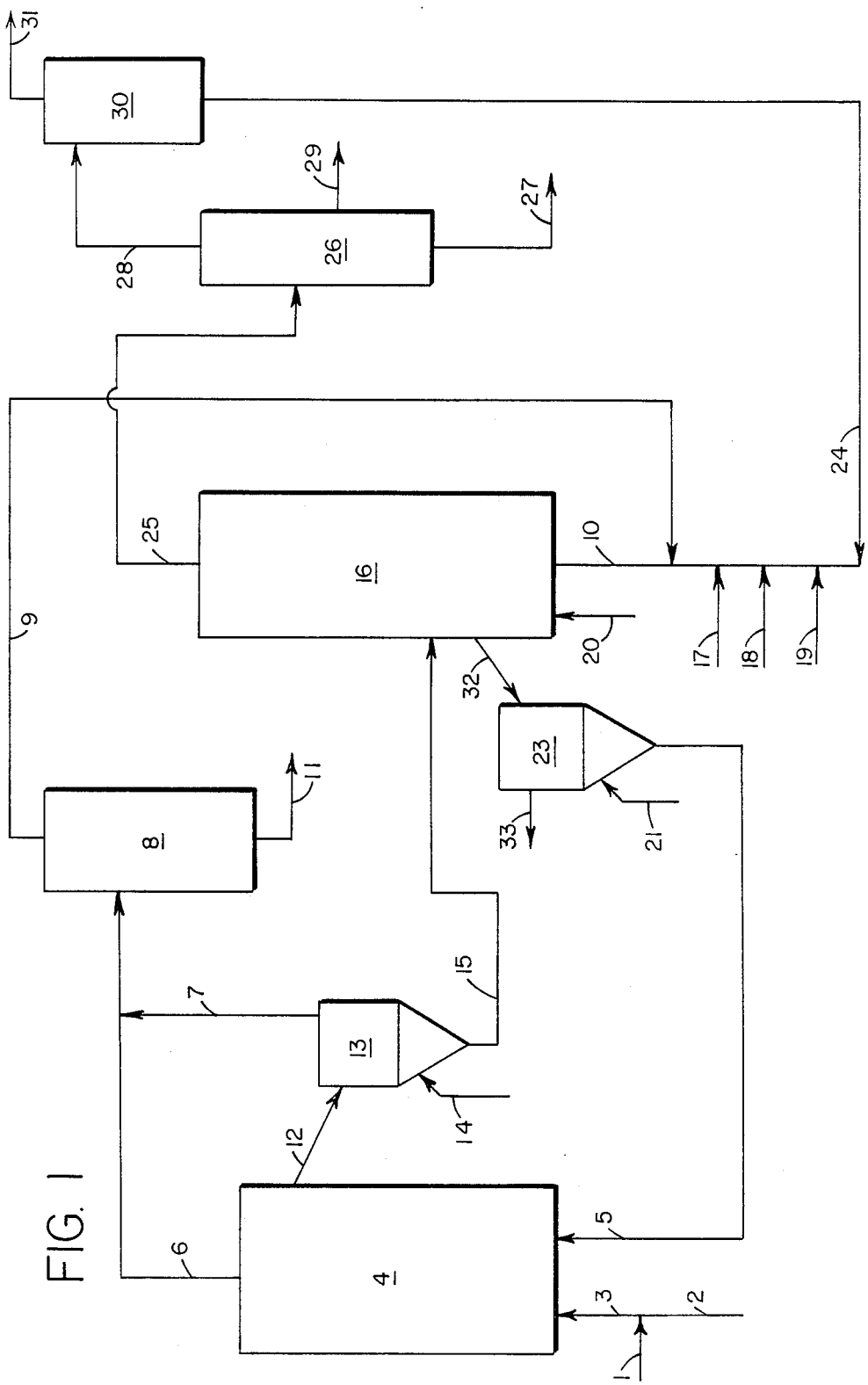

Referring to the attached FIG. 1 an iso-olefin-containing olefinic stream 1 is mixed with a methanol stream 2 in the ratio of from about 1.0 mols methanol per 1.0 mols iso-olefin to 2.0 mols methanol per 1.0 mols iso-olefin. The iso-olefin/methanol mixture 3 is charged to a reactor 4 along with deactivated catalyst 5. The reactor 4 is maintained at between −20° and 250° C., preferably between about 50° and 120° C. and between 50 psig and 5000 psig, preferably around about 200 psig. The reactor 4 is sized for an iso-olefin/catalyst weight hourly space velocity of between about 10 and about 30. (Weight hourly space velocity is defined as the weight of the specified reactant per unit time divided by the weight of the catalyst.)

The reactor product stream 6 is mixed with slurry settler overheads 7 and charged to a distillation tower 8. The overhead product 9 from distillation tower 8 is rich in olefins. This olefin-rich overhead stream 9 becomes a constituent of the heterogeneous catalytic alkylation reactor feed 10. The distillation tower bottom stream 11 consists of methanol and alkyl tert-alkyl ether and is further separated to recover substantially pure alkyl tert-alkyl ether.

A slip stream 12 of reactivated catalyst together with a solution of reactants is withdrawn from reactor 4. Isoparaffins or a mixture of normal paraffins and olefins 14 is charged to the slurry settler 13 to enhance solid/liquid separation. Reactivated catalyst 15 flows to an alkylation reactor 16.

Alkylation reactor charge 10 consists of the following:

TABLE 1

| Stream Number | Stream Name |
|---|---|
| 9 | Distillation Tower 8 overhead stream |
| 17 | Normal Olefinic and Paraffinic Fresh Feed |
| 18 | Normal Olefinic and Paraffinic Fresh Feed |
| 19 | Isoparaffinic Fresh Feed |

TABLE 1-continued

| Stream Number | Stream Name |
| --- | --- |
| 24 | Isoparaffins From Distillation Tower 30 |

The flow rates and compositions of the alkylation reactor charge streams are regulated to maintain an isoparaffin to olefin ratio of between about 3 to 30, and the olefin weight hourly space velocity at between about 0.5 and 10.0.

Boron trifluoride 20 is charged to the alkylation reactor 16 to promote acidic catalyst activity. The boron trifluoride charge rate is maintained at between approximately 0.1 to 10 pounds boron trifluoride per 100 pounds of hydrocarbon feed, preferably at about 1 pound boron trifluoride per 100 pounds of hydrocarbon feed.

A slip stream slurry of deactivated catalyst 32 is withdrawn from the alkylation reactor 16 and fed to the deactivated catalyst slurry settler 23. The slurry is purged with methanol 21. Methanol with trace boron trifluoride 33 is withdrawn from the top of the slurry settler. The boron trifluoride/methanol mixture may then be separated by distillation. The purified boron trifluoride stream may be recycled to the alkylation reactor 16 and the methanol may be recycled to the alkyl tertiary-alkyl ether synthesis reactor 4.

Deactivated catalyst 5 flows to the alkyl tertiary-alkyl ether synthesis reactor 4 for reactivation. The alkylation reactor product 25 flows to a distillation tower 26. Three streams leave the distillation tower 26. The bottom stream 27 is the finished alkylate product. The side draw 29 is rich in the heavier normal paraffins. The overhead stream 28 is fed to a second distillation tower 30. The second distillation tower overhead product 31 consists of lighter normal paraffins with trace amounts of boron trifluoride. The bottoms product 24 consists of isoparaffins, which is recycled to the alkylation reactor charge stream 10. The alkylation reactor 16 is maintained at $-20°$ to $250°$ C., preferably between about $0°$ to $40°$ C. and between about 50 psig to 5000 psig, preferably between about 100 to 200 psig.

What is claimed is:

1. A process for alkylation of isoparaffins with olefins and for the preparation of an alkyl tertiary-alkyl ether comprising the steps of:
   a. reacting an isoparaffin containing from 4 to 6 carbon atoms with an olefin containing from 2 to 6 carbon atoms at from about $-20°$ C. to about $250°$ C. and at a pressure in the range of 50 psig to about 5000 psig employing a reaction mixture wherein the molar ratio of said isoparaffin to said olefin is from 3 to 30 in contact with a composite catalyst comprising a Lewis acid and a zeolite catalyst which is capable of absorbing 2,2,4-trimethylpentane wherein said zeolite catalyst becomes deactivated over time when exposed to the isoparaffin/olefin reaction mixture, and
   b. separting said deactivated zeolite catalyst from said isoparaffin/olefin reaction mixture, and
   c. reacting between about $20°$ and $250°$ C. and between about 50 psig and 5000 psig a primary alcohol with an olefin having a double bond on a tertiary carbon atom in the presence of said deactivated zeolite catalyst, whereby said catalyst is reactivated, and an alkyl tertiary-alkyl ether is evolved, and
   d. separating said reactivated catalyst from said primary alcohol/olefin/alkyl tertiary-alkyl ether mixture, and
   e. recycling said reactivated catalyst to contact said isoparaffin/olefin mixture as recited in step (a).

2. The process of claim 1, wherein said zeolite catalyst has a Constraint Index of from about 0.4 to 12 and a silica/alumina mole ratio between about 5 and about 150.

3. The process of claim 1, wherein said isoparaffin contains from 4 to 5 carbon atoms and said olefin contains from 2 to 5 carbon atoms.

4. The process of claim 2, wherein said isoparaffin contains from 4 to 5 carbon atoms and said olefin contains from 2 to 5 carbon atoms.

5. The process of claim 1 wherein the Lewis acid is selected from the group consisting of $BF_3$, $SbF_5$, and $AlCl_3$.

6. The process of claim 1 wherein the zeolite is selected from the group consisting of ZSM-20, ZSM-3, ZSM-18, zeolite Beta, faujasite, mordenite, zeolite Y, and the rare earth metal containing forms of the above.

7. The process of claim 1 wherein the zeolite is zeolite Beta.

8. The process of claim 1 wherein the zeolite is contained in a matrix.

9. The process of claim 1 wherein the reaction is conducted under sufficient pressure to maintain at least one of the reactants in a liquid phase.

10. The process of claim 1 wherein the isoparaffin is isobutane and the olefin is butene.

11. The process of claim 1 wherein the isoparaffin is isobutane and the olefin is propene.

12. The process of claim 5 wherein the zeolite is contained in a matrix.

13. The process of claim 6 wherein the zeolite is contained in a matrix.

* * * * *